United States Patent [19]

Inman et al.

[11] Patent Number: 4,578,063
[45] Date of Patent: Mar. 25, 1986

[54] CENTRAL VENOUS CATHETER

[75] Inventors: Charles M. Inman, Flagstaff; Donald J. Stone, Rimrock, both of Ariz.

[73] Assignee: W. L. Gore & Assoc., Inc., Newark, Del.

[21] Appl. No.: 650,722

[22] Filed: Sep. 14, 1984

[51] Int. Cl.$^4$ .............................................. A61M 5/00
[52] U.S. Cl. ................................... 604/175; 604/244
[58] Field of Search ............ 604/175, 174, 891, 8–10, 604/244

[56] References Cited

U.S. PATENT DOCUMENTS

| | | | |
|---|---|---|---|
| 3,402,710 | 9/1968 | Paleschuck | 604/175 X |
| 4,015,601 | 4/1977 | Bokros et al. | 604/175 |
| 4,164,221 | 8/1979 | Bentley | 604/175 X |
| 4,321,914 | 3/1982 | Bergovac et al. | 604/896 X |
| 4,417,888 | 11/1983 | Consentino | 604/175 |
| 4,488,877 | 12/1984 | Klein et al. | 604/175 |

*Primary Examiner*—Stephen C. Pellegrino
*Attorney, Agent, or Firm*—Mortenson & Uebler

[57] ABSTRACT

A percutaneous implant device is provided which is stable, biocompatible, substantially infection-free and provides a long-term port of entry into the body, the device having an easy-to-use, effective, contamination-resistant capping and valving system for the exchange of fluids into and out of the body. The device comprises a nonporous biocompatible conduit having an attached flange, the flange having a top and a bottom. In the preferred embodiment, at the top of the flange, where the flange and conduit connect, the conduit emerges from the flange, necks inwardly and then flares outwardly forming an hourglass configuration. Above this neck the conduit forms substantially a right-angle bend, the conduit then extending substantially parallel to the skin. The device is implanted in the body such that the flange is below the surface of the skin. The flange preferably is covered with a porous, biologically inert material which permits growth of connective tissue and vascularization. Within the neck portion of the device, the inside diameter of the conduit is increased resulting in a decrease of the conduit wall thickness in the neck region creating a point of flexion which acts as a cushion to absorb forces that could otherwise disrupt the skin/device interface. By reason of the bend in the conduit, the conduit can be grasped and held firmly while pressure is applied parallel to the skin surface to insert a needle into or apply a cover cap to the conduit. Removable protective cap means and blunt insertion needle assembly means are provided, as well as suitable valving and connector means, providing a connection between the bottom of the flange and any internal conduit.

20 Claims, 16 Drawing Figures

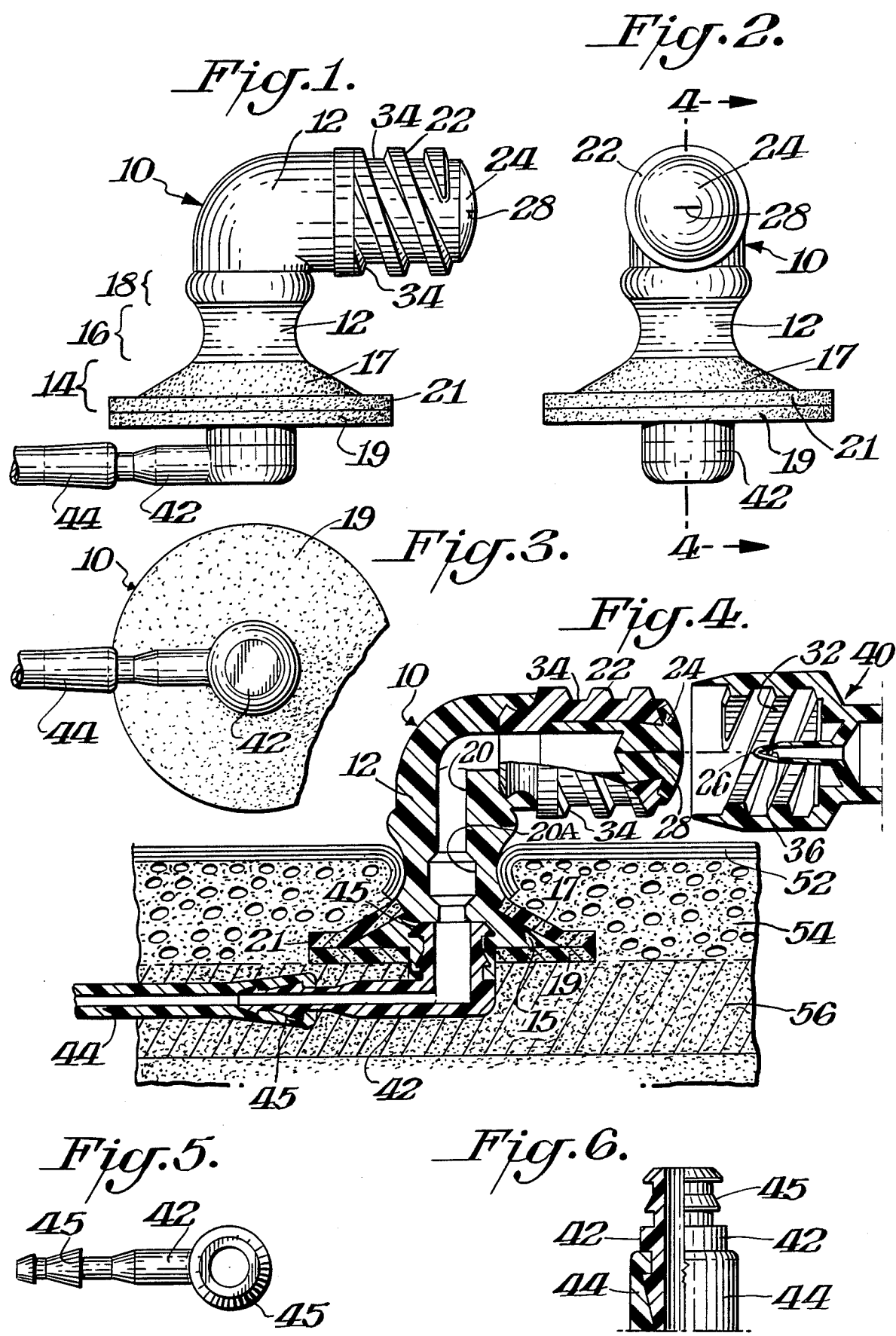

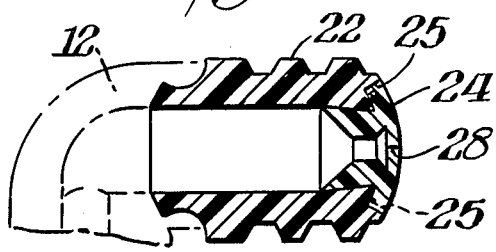
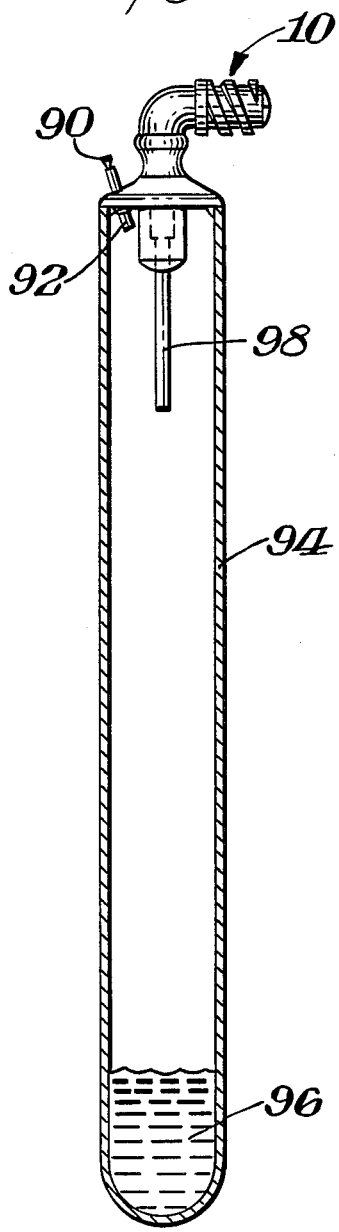
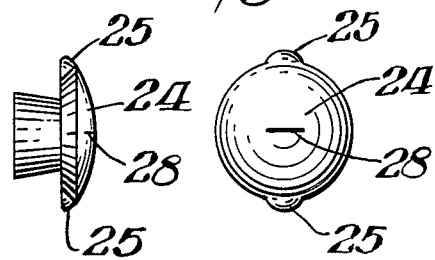
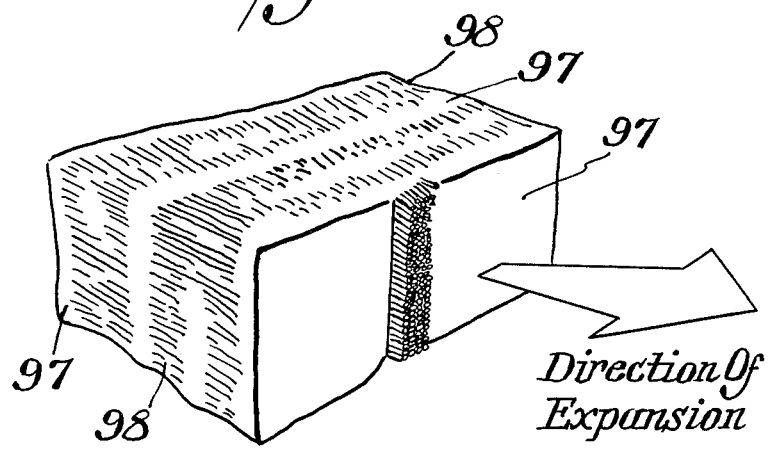

CENTRAL VENOUS CATHETER

FIELD OF THE INVENTION

This invention relates to an improved implantable percutaneous device, in particular to an improved capping and valving system for a low profile percutaneous device which prevents foreign material and microorganisms from entering the body through the lumen of the conduits of such devices.

BACKGROUND OF THE INVENTION

A percutaneous implant is an object, foreign to the body, that has been placed through the skin to allow a port of entry to inner body spaces and structures. Temporary percutaneous access is required for a wide variety of procedures such as intra-venous fluid administration and hemodialysis. A number of these procedures also require chronic access. Specific examples of applications which benefit from a chronic percutaneous port include hemodialysis access, peritoneal dialysis access, power supply leads and fluid connections for artificial organs, charging for cardiac pacemakers, neuroelectric stimulation of nerves and/or muscles, artificial stimulation and monitoring in various brain implants.

Acute percutaneous access is routinely accomplished with devices constructed of silicone, polypropylene and polyurethane. These devices serve as a mechanism by which to gain blood access, wound drainage and many other applications. The chronic use of such devices, however, commonly results in infection and/or encapsulation of the device by the epidermis. Past attempts to overcome these problems have included a variety of devices constructed of various materials and have included both rigid and flexible devices.

Percutaneous implant devices are designed to prevent bacteria from entering the body through skin exit site areas. The standard design for percutaneous implants consists of a central conduit surrounded by an attached flange. The flange can be a rigid or flexible disk that is covered with a flexible biocompatible material such as expanded polytetrafluoroethylene (PTFE), polyester and polyamide velours, polyurethane, polypropylene and polyethylene. These biocompatible materials are normally porous in structure to allow for sufficient connective tissue ingrowth and anchorage. Epithelium is directed downward allowing for contact epithelium inhibition and forms a bacterial seal with connective tissue preventing the evagination and extrusion of the percutaneous implant device. Connective tissue ingrowth and vascularization are designed to form a barrier at the skin exit site to prevent foreign material and microorganisms from entering the body.

There is a need for an easily handled and effective system for preventing foreign material and microorganisms from entering through the lumen, a major problem when the exchange of fluids into or out of the body is required. Most percutaneous implants contain a central conduit of a biocompatible material that is attached to the flange ingrowth segment of the device. The common conduit materials are polydimethylsiloxane (silcone rubber), polyurethane, polyethylene, polypropylene, polytetrafluoroethylene, polycarbonate, titanium and carbon. This conduit extends through the body and is capped by a variety of means. When filling the conduit with materials such as wires, fibers and various leads, contamination is not a great problem because these materials can be sealed or adhered solidly into the lumen of the conduit. This solid barrier in the lumen allows for a variety of attachment mechanisms such as magnets, screw on devices and friction fit apparatus to be utilized as connection and disconnection systems. Because these conduits are not open conduits, special connectors that act as a mechanical fuse and separate at the interface without damage to the interface have been developed as set forth in U.S. Pat. No. 4,004,298.

Openings through the flange ingrowth segment are provided to allow for the passage of a variety of tubings, catheters and conduits. These conduits are permanently attached to the flange portion by molding, sealing or adhesion or they can be temporarily placed through the flange portion as shown in U.S. Pat. No. 3,402,710. Through the lumen of these various conduits, fluids are allowed to flow in and out of the body. At the exterior, proximal end of these conduits, outside the body, standard luer lock fittings and adapters can be secured. The potential for an exposed lumen in the conduit can occur anytime a connection or disconnection is made with an additional fluid line, such as an intravenous line. Any breaks or holes in any part of the system also lead to an exposed lumen. Any time the conduit is opened in any manner, the introduction of infection may result, leading to septicemea, emboli, backbleeding or backflow of other vital body fluids (Coppa, G. F., Gouge, T. H., and Hofstetter, S. R.: Air Embolism: A Lethal but Preventable Complication of Subclavian Vein Catheterization. *J. Parenteral & Enternal Nutrition* 5(2):166–168, Mar/Apr 1981).

Skin interface disruption can also result when conduits protrude from the body. The forces disrupting the interface are normally caused by actions such as twisting, tugging and pulling while handling the external portion of the conduit during connection and disconnection (Von Recum, A. F., and Park, J. B.: Permanent Percutaneous Devices. *CPC Critical Reviews in Bioengineering* 5(1):37–77, 1981). Without proper dressings and taping of the conduit down to the skin, tightness of clothing can also irritate the interface site presenting additional trauma (Erlich, L. F., and Powell, S. L.: Care of the patient with a Gore-Tex Peritoneal Dialysis Catheter. *Dialysis & Transplantation* 12(8):572–577, Aug. 1983).

Because of the need to physically seal an open conduit during connections and disconnections, mechanical damage can result, necessitating repairs or the eventual removal of the device. The same type of damage that occurs to standard catheters can occur to any type of conduit placed through a percutaneous device because of the necessity to physically seal the lumen during connections and disconnections (Gulley, R. M., Hawk, N.: Rupture of Indwelling Venous Catheters. *J Parenteral & Enteral Nutrition* 7(2):184–185, Mar/Apr, 1983).

Prior art has disclosed a percutaneous implant device for drug injection with a normally closed value in a passageway, for administration of medication, e.g. U.S. Pat. No. 3,783,868 and 4,321,914. However, the known prior art does not address the complications of skin exit disruptions due to forces applied to the exterior portions of the conduit during connections and disconnections.

The solution to these problems is found in the improved implant device of this invention that utilizes design advantages, the physical properties of the materials used and a unique handling system.

SUMMARY OF THE INVENTION

A percutaneous implant device to provide a port of entry into the body is provided comprising a nonporous, biocompatible conduit having an upper inlet opening and a lower attached flange, the flange having a top with a continuously curved perimeter and a continuously curved side wall which tapers to a bottom wall having a continuously curved perimeter of larger diameter than said top, and having a central opening therethrough extending from said top through said flange to said bottom wall, said conduit extending from the top of the attached flange and having an angle bend just above said flange which, in use, extends at an angle to the skin, from the bend location to the conduit inlet.

The preferred device comprises:

(A) a nonporous, biocompatible conduit having an attached flange, the flange having a top with a continuously curved perimeter and a continuously curved side wall which tapers to a bottom wall having a continuously curved perimeter of larger diameter than said top, and a central opening therethrough extending from the top through the flange to the bottom wall, (B) the conduit extending from the top of the flange first necking inwardly and then flaring outwardly forming an hourglass configuration, (C) the conduit having a substantially right angle bend above the hourglass configuration which, in use, extends substantially parallel to the skin, from the bend portion to the conduit inlet, (D) the conduit, within a part of the hourglass portion, having an inside diameter which is larger than the inside diameter of the remainder of the conduit, thereby providing a decreased conduit wall thickness at the hourglass configuration, (E) an upper skirt and a bottom skirt formed of expanded, porous polytetrafluoroethylene having nodes and fibrils, with average fibril length greater than or about 60 microns to permit the in-growth of epidermal and connective tissue, (i) the upper skirt attached to the side wall of the flange and extending from the perimeter of the bottom wall to just below the minimum diameter of the hourglass configuration, such that, in use, the upper skirt is place subcutaneously and, (ii) the lower skirt being in laminar contact with the bottom wall and connected to the upper skirt adjacent the perimeter of the bottom wall.

The porous, expanded polytetrafluoroethylene preferably has average fibril length greater than about 60 microns, ethanol bubble points less than about 2.0 psi, ethanol mean flow pressure less than about 10 psi, and density less than about 1 gram/cc. Most preferably, the expanded PTFE has average fibril length greater than about 100 microns, ethanol bubble point less than about 0.75 psi, ethanol mean flow pressure less than 3.0 psi and density in the range of about 0.3 to about 1.0 grams/cc. Removable cap means and removable blunt insertion needle assembly means are provided. Attachment means for attaching the cap and blunt needle assembly comprise a male two start acme thread about the conduit. This thread engages the female two start acme thread port of the cover cap or the blunt insertion needle assembly means. A mechanical connecting apparatus is incorporated in the central opening of the flange providing connecting means between the bottom of the flange and an internal conduit. The conduit and flange are preferably formed of medical grade, biocompatible polydimethylsiloxane elastomer. A self-sealing face valve is located at the opening of the conduit.

BRIEF DESCRIPTION OF THE DRAWINGS

FIG. 1 is a side elevation of the percutaneous implant device of this invention.

FIG. 2 is a front elevation of the device.

FIG. 3 is a bottom plan view of the device.

FIG. 4 is a cross-sectional view of the device implanted in a body taken along line 4—4 of FIG. 2.

FIG. 4A shows a preferred design of a self-sealing face valve inserted into the conduit inlet of the device, in cross-section.

FIG. 4B is a front elevation of the valve shown in FIG. 4A and FIG. 4C is a side elevation thereof.

FIG. 5 is a top plan view of the connector used with this device.

FIG. 6 is an elevational view of an alternate connector, partly in cross-section connected in-line to an internal conduit.

FIG. 12 shows schematically the apparatus used in conducting the bacterial challenge testing for the catheter of the invention.

FIG. 13 is a schematic view, many times magnified, of the microstructure of expanded polytetrafluoroethylene.

Figure 7:
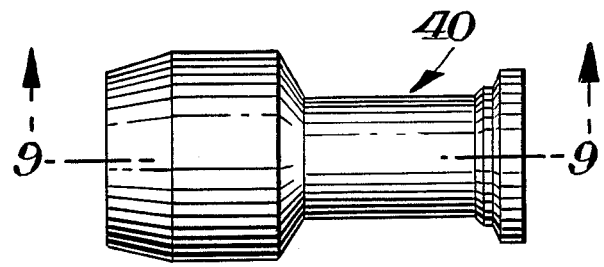
FIG. 7 is a side elevation of a blunt needle assembly to be used with the device of the invention.

DETAILED DESCRIPTION OF THE INVENTION AND PREFERRED EMBODIMENTS WITH REFERENCE TO THE DRAWINGS

A percutaneous implant device is provided which is stable, biocompatible, substantially infection-free and provides a long-term port of entry into the body, the device having an easy-to-use, effective, contamination-resistant capping and valving system for the exchange of fluids into and out of the body. The device comprises a nonporous bicompatible conduit having an attached flange, the flange having a top and bottom. In the preferred embodiment, at the top of the flange, where the flange and conduit connect, the conduit emerges from the flange, necks inwardly and then flares outwardly forming an hourglass configuration. Above this neck the conduit forms substantially a right-angle bend, the conduit then extending substantially parallel to the skin. The device is implanted in the body such that the flange is below the surface of the skin. The flange preferably is covered with a porous, biologically inert material which permits growth of connective tissue and vascularization. Within the neck portion of the device, the inside diameter of the conduit is increased resulting in a decrease of the conduit wall thickness in the neck region creating a point of flexion which acts as a cushion to absorb forces that could otherwise disrupt the skin/device interface. By reason of the bend in the conduit, the conduit can be grasped and held firmly while pressure is applied parallel to the skin surface to insert a needle into or apply a cover cap to the conduit. Removable protective cap means and blunt insertion needle assembly means are provided, as well as suitable valving and connector means, providing a connection between the bottom of the flange and any internal conduit.

A percutaneous device 10 of the present invention is shown in FIG. 1 and comprises biocompatible conduit 12 with an attached flange 14. At the top of the flange, where the flange and conduit connect, the conduit 12 emerges from the flange and the exterior of the conduit flares inward and then outward forming an hourglass or neck configuration 16. The convex section of the conduit 18, FIG. 1, is termed the collar portion of the device.

Above the collar 18, on the exterior side of the flange, the conduit bends at an angle, preferably in a direction that will run substantially parallel to the skin externally.

The flange is covered with a porous biologically inert material comprised of expanded polytetrafluoroethylene (PTFE). Expanded PTFE has a microstructure which consists of a three-dimensional matrix of nodes connected by fibrils. This porous microstructure allows for the ingrowth of connective tissue and vascularization. The top and bottom of the flange are covered with this porous skirt material 17, 19. The top skirt 17 is adhered to the top of the flange from the upper portion where the conduit and flange meet, past the outer diameter of the flange. The bottom skirt 19 is adhered to the bottom of the flange, also extending beyond the maximum diameter of the flange. The bottom cover 19 and top skirt 17 materials are bonded together beyond the outer diameter of the flange in the line 21 formed between the covers. Epidermal cells may extend to and attach to connective tissue within the porous PTFE cover material.

It is believed that other porous biocompatible materials could be used. The porous material must allow rapid ingrowth of connective tissue to inhibit the apical migration of epithelium along the surface of the material. Preferably the porous material is soft and flexible. Suitable biocompatible materials which could be made porous include, but are not limited to, silicones, polyurethanes, polyethylenes, polysulfones, polyacrylics, polycarboxylates, polyesters, polypropylenes, poly(hydroxyethylmethacrylates), and perfluorinated polymers such as fluorinated ethylene propylene, as well as polytetrafluoroethylene.

The above-mentioned materials may be made porous by techniques known to those skilled in the art which will render the materials capable of supporting connective tissue ingrowth while preventing apical migration of epithelium. Such tecniques include, but are not limited to, sintering carefully controlled sizes of polymer beads; combining the materials with a partially resorbable implant that would resorb or could be resorbed, in vivo or in vitro, to leave a porous surface; weaving or knitting fibers together to form a fabric-like material; or using a foaming agent during processing to cause bubbles to form and leave pores as the material hardens.

The porous material may be treated or filled with biologically active substances such as sntibiotics, fibrin, thrombin, and collagen. These substances may enhance connective tissue formation within the porous material and inhibit infection during healing.

The porous material of the preferred embodiment, as stated, is expanded polytetrafluoroethylene (expanded PTFE). Expanded PTFE is an extremely inert and biocompatible material with a history of medical implant use. U.S. Pat. Nos. 3,953,566 and 4,187,390, the disclosures of which are incorporated herein by reference, teach methods for producing expanded PTFE and characterizing its porous microstructure. The porous structure of expanded PTFE is further schematically illustrated in FIG. 13. The microstructure of expanded PTFE is a three-dimensional matrix of nodes 97, connected by fibrils 98. The pore size of expanded PTFE can be characterized by determining the bubble point and the mean flow pressure of the material. Bubble point and mean flow pressure are measured according to the American Society for Testing and Materials Standard F316-80, using ethanol.

The density of expanded PTFE determines the amount of void space in the material which may become ingrown with connective tissue. The density of expanded PTFE is the ratio of the mass of a given sample of expanded PTFE to its volume.

The fibril length of expanded PTFE is defined herein as the average of ten measurements of distances between nodes connected by fibrils in the direction of expansion. In order to measure the average fibril length of expanded PTFE, two parallel lines are drawn across a photomicrograph of about 40 to 50 times magnification of the surface of the material so as to divide the photgraph into three equal areas. If the material has been uniaxially expanded, these lines are drawn in the direction of expansion, i.e. direction of longitudinal orientation of fibrils as shown in FIG. 13. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. If the material is expanded in more than one direction, the lines are drawn and fibril lengths measured as above, except when a node is not attached by fibrils to a node intersecting the drawn line. In that case, the fibril length from the node to a node which creates the least angle with the drawn line is measured along the fibril's axial orientation. The ten measurements obtained by this method are then averaged to obtain the average fibril length of the material.

Materials with average fibril lengths greater than about 60 microns, preferably greater than about 100 microns, ethanol bubble points of less than about 2.0 psi, preferably less than about 0.75 psi, ethanol mean flow pressure less than about 10 psi, preferably less than about 3.0 psi, and densities less than about 1 gram/cc and preferably about 0.3 to about 0.1 gram/cc enhance connective tissue ingrowth and are therefore most preferred for use in the present invention.

When expanded PTFE is used as the porous material, a number of nodes 97 may pass through the wall thickness of the expanded PTFE, as illustrated in FIG. 13, which may provide channels for tissue ingrowth and a wall resistant to crushing. In the preferred embodiments, an expanded PTFE skin interface with a wall thickness of approximately 1 mm is used. It should be understood that one side may be laminated which will tend to close the pores not allowing for tissue ingrowth. This portion is not intended for tissue ingrowth and will not pass ethanol bubble point testing described above.

The device of the present invention provides for the central conduit 12 to contain a capping and valving system 24 which is an integral part of the device. The preferred material for the conduit is medical grade, biocompatible and inert polydimethylsiloxane. The conduit emerges from the epidermis perpendicular to the skin surface. In the section of conduit that emerges from the epidermis perpendicular to the skin surface, referred to as the neck 16, a point of flexion is made at the minimum diameter. Increasing the inner diameter of the conduit by several thousandths of an inch inside the neck 16 results in reducing the wall thickness by several thousandths of an inch. The reduction in wall thickness over a length of approximately 0.100 inches* along the conduit creates this point of flexion. This point of flexion is preferably created approximately 0.050 inches from the point where the external portion of the conduit 12 connects with the flange ingrowth segment of the device. This flex point serves as a cushion to absorb and redirect forces that could otherwise disrupt the skin/device interface. Following the conduit exteriorly past the said flex point, a bend in the conduit positions the conduit so that it runs parallel to the skin surface for a distance of an inch. The bend in the conduit absorbs some or all of the forces that are generated when pressure is applied. Forces are normally required to attach various apparatus to low profile implant devices which results in the disruption of the living tissue from the ingrowth segment of the device. By positioning a permanent bend in the conduit approximately 0.230 inches from the point of flexion, the conduit can be grasped and held firm, while pressure is applied parallel to the skin to insert a needle or apply the cover cap to the external end of the conduit. Forces applied to the exterior portion of the conduit will be absorbed or redirected by the flex point allowing the conduit to bend, due to weakness of the wall structure created by this point of flexion. Preferably the forces that would otherwise disrupt the flange living tissue interface will be absorbed by the flexible conduit and flex points. A biocompatible thermoplastic polymer mounting ring 22 is permanently adhered to the external end of the conduit 12. This rigid material containing an external male two start acme thread 34 which allows for the end of the conduit to be connected to a removable protective cap and a removable blunt insertion needle assembly. *All dimensions given are exemplary and/or preferred.

Connector 42 shown in FIG. 1 serves to connect the implant device 10 to an internal body conduit 44.

FIG. 2, in a front elevation, shows the device 10 and face valve 24 having slit 28 inserted into the exterior end of the device. Slit 28 allows insertion of blunt needle apparatus. Also shown in FIG. 2 are the flange covers 17 and 19, bonded at common area of contact 21, and connector 42.

FIG. 3 shows a bottom plan view of the implant device 10 whose bottom is covered with the expanded, porous PTFE cover 19 connected via connector 42 to internal body conduit 44.

FIG. 4 shows a corss-sectional view of the assembly of this invention, implanted in a body, taken substantially along the line 4—4 of FIG. 2.

The device is placed in the body so the portion of the conduit called the neck 16 is placed through the skin comprising the epidermis, 52, the dermis, 54, and subcutaneous tissue, 56, in such a manner as to leave the flange below the surface of the skin. The outer diameter of the neck portion of the conduit provides a continuously curving geometry which encourages and directs epidermal cells to grow in a direction toward the flange.

A flexible, normally closed, convex, cleanable face valve 24 is attached at the external end of the conduit. This valve is preferably a selfsealing slit valve, comprised of a medically acceptable elastomeric polymer. This valve is physically opened by means of a blunt insertion needle. Upon attachment of the insertion needle assembly 40 to the exterior of the device, the convex cleanable face valve is physically opened. In the event the insertion needle assembly 40 is removed, the face valve will close and seal. This valving system eliminates the need for greater lengths of external conduits and tubing. Elimination of dangling conduits reduces the potential number of incidences of skin exit disruptions by removing unwieldly, cumbersome and often heavy capping and valving mechanisms which are at the ends of these conduits.

A preferred valve design is illustrated in FIGS. 4A and 4B. As the infusion needle penetrates through the slit valve shown, it passes through a concentric type seal which snuggly captures the needle except for the tip. This seal prevents leakage around the needle while in place through the slit. As shown in FIGS. 4B and 4C, this valve is molded with additional material 25 above and below slit 28. When inserted into the mounting ring 22, the compression of the face valve by the mounting ring provides a preferred stress on the slit in the valve as a result of the additional material 25, resulting in preferred forces directed at keeping the slit 28 closed.

As shown in FIG. 4, at the bottom of the flange segment of the device, the lumen of the conduit is designed to allow for the secure insertion of additional conduit material 42. Preferably, a biocompatible thermoplastic polymer connector with barbed fittings 45 on each end can be used to connect additional tubing 44, ingrowth segments or other apparatus. This thermoplastic connector can be snapped into the device utilizing built-in silicone O-rings in the device for a secure pressure fit that eliminates leakage. With this pressurized fit, the connector can swivel to allow proper placement of the internal conduit during implantation. The connector 42 can also be securely adhered in place. The connector 42 can protrude from the device perpendicularly or can have various bends and angles depending on the appropriate placement of the internal apparatus.

By eliminating the valves in the device and the internal connector, the passageway of the device can be placed with electrical wires, power supply units, such as rechargable batteries, and fiber optic strands.

The percutaneous implant device 10 comprises conduit 12 having a collar 18, a neck portion 16 and a flange portion 14, all preferably made of silicone. The device is implanted so that the flange is placed under the skin and the neck and collar of the conduit protrudes through and above the skin as shown in FIG. 4. The height of the conduit, from the bottom of the flange including the PTFE cover material 19 to the transition point where the bend in the conduit begins, is approximately 0.530 inches. The collar portion of the conduit protrudes through the epidermal layer 52 and guides the epidermal cells along the neck portion towards the porous PTFE material 17. The collar has a diameter of about 0.360 inch with a range from 0.250 inch to 2 inches. The neck portion is the narrowest part of the conduit, approximately 0.260 inch in diameter. As the neck flares outward and is directed towards the flange, it reaches a maximum diameter at the base of approximately 0.306 inch. The conduit is directed inward at this point over a distance of about 0.035 inch. At the end of this indentation, the flange begins and the diameter is about 0.266 inch at this point. The difference in diameters between the neck base and the start of the flange forms an indentation allowing a snug fit for the expanded PTFE cover. The flange has a maximum diameter of approximately 0.600 inch.

The lumen 20 of the conduit from the collar to the base of the neck is about 0.100 inch in diameter, excluding the point of flexion. In the middle of the neck, a point of flexion 20A is created by increasing the inner diameter of the conduit to about 0.130 inch for a height of 0.100 inch. This point of flexion starts approximately about 0.050 inch from the base of the neck and flange. The point of flexion 20A is ideally located in the middle of the neck.

The implant device 10 has a rigid mounting ring 22, preferably polycarbonate, which is bonded to the conduit 12. Adhered inside the front portion of the rigid mounting ring 22 is the cleanable, smooth, convex face valve 24, preferably silicone. As the blunt needle 26 of the injection needle assembly 40 is inserted to physically open the self-sealing slit 28 of the silicone face valve, the injection needle assembly threads 32 are screwed onto the external mounting ring thread connections 34 and held. When the face valve 24 is physically opened, the lumen of the device 20 is exposed. As fluid is introduced and flows through the lumen of the insertion needle 26, it flows through the side openings 36 of the blunt needle 26 and into the lumen 20 of the device. The fluid can flow through the connector 42 into the internal conduit 44 to the desired location.

The rigid mounting ring 22 may be treated by a spray or coating process of monosiloxane SiO$_2$ (U.S. Pat. No. 3,986,977). This coated surface of the ring allows for the bonding of the silicone conduit 12 to the ring by means of a silicone adhesive.

The mounting ring 22 may be from about 0.100 inch to 1.0 inch long. Preferably the mounting ring is about 0.60 inch long. The inner diameter of the ring may be from about 0.10 inch to 0.3 inch, the outer diameter from about 0.2 inch to 0.5 inch. Preferably the inner diameter is about 0.200 inch, and the outer diameter about 0.312 inch. The external threads 34 on the mounting ring can be from about 0.030 inch to 0.045 inch wide. Preferably the width of the threads is about 0.038 inch. The length of the threads cover a distance of about 0.280 inch to 0.310 inch. Preferably the threads cover a distance of 0.290 inch.

The insertion needle assembly 40 can be made from several different materials such as polycarbonate, polysulfone, polypropylene, polyamides, polyurethane, stainless steel, and polyethylene. The inner diameter of the needle assembly which encompasses the mounting ring may be 0.2 inch to 0.5 inch. Preferably the inner diameters is 0.314 inch to provide a tight, secure seal while placed over the mounting ring. The outer diameter of this end can be 0.25 inch to 0.600 inch but preferably is 0.375 inch. The threads 32 can have a width of 0.030 inch to 0.045 inch. Preferably the width of the threads are 0.038 inch. The length of the threads should cover a distance of 0.280 inch to 0.310 inch. Preferably the threads cover a distance of 0.290 inch. The threads have a depth preferably of 0.0255 inch. The pitch of the threads is preferably 5 threads per inch. At the end of the needle assembly is a 2 degree friction taper fit for added security.

The length of the needle can be from about 0.080 inch to 0.380 inch. Preferably the length of the needle is 0.240 inch. The length of the needle and valve determines whether the face valve is utilized in a partially opened mode or a completely opened mode. This affects the pressure at which fluids are injected. The lumen of the needle can be from 0.005 inch to 0.150 inch. The needle inner diameter is dependent on the application and the flow requirements. Dialysis would require a different flow volume than parenteral nutrition therapy. The diameter of the needle is dependent upon the inner diameter of the needle. Preferably a wall thickness for the needle should be about 0.015 inch, but can be about 0.010 inch to 0.040 inch.

The inner diameter of the assembly can be from about 0.050 inch to 0.300 inch. Preferably the inner diameter is about 0.170 inch with a 2 degree taper that will accomodate standard luer lock friction fits. At the end of the needle assembly is a pair of projecting parts that will fit standard luer lock female apparatus.

The overall length of the needle assembly can be from about 0.400 inch to 1.50 inch. Preferably the overall length is about 0.750 inch.

The protective cover cap can have an inner diameter of about 0.200 inch to 0.500 inch. Preferably the inner diameter is about 0.314 inch to ensure a secure fit over the mounting ring. The wall thickness of the protective cap cover from the concave portion to the edge of the cap can be about 0.005 inch to 0.100 inch with the internal threads 50 being from about 0.030 inch to 0.045 inch. Preferably the wall thickness should be about 0.030 inch, while the thread should be about 0.038 inch wide. The length of the threads should cover a distance of 0.280 inch to 0.310 inch with a pitch of 5 threads per inch. Preferably the threads cover a distance of 0.290 inch. Preferably the wall thickness should be about 0.030 inch. The overall length of the cap can be from about 0.250 inch to 0.750 inch. To prevent excessive contact with clothing, dressings, etc., it is preferable to have the length of 0.515 inch which still provides ease of handling while keeping a low profile. The protective cap cover can be molded, machined, or fabricated out of such materials as polypropylene, polycarbonate, polysulfone, polyethylene, polyamides, polyurethane or stainless steel.

The connector 42 should be made out of biocompatible, nonporous, rigid or semi-rigid material such as polytetrafluoroethylene, polycarbonate, polysulfone, polypropylene or polyurethane. The outer diameter can be 0.200 inch to 0.500 inch while the inner diameter can be 0.005 inch to 0.150 inch. The diameters of the connector should coincide with the diameter of the lumen of the needle to be used to allow for sufficient flow all through the device. The wall thickness of the connector can be from about 0.010 inch to 0.200 inch. Preferably the wall thickness is 0.025 inch. The diameter of the barbs 45 on the upper end of the connector 42 range from about 0.100 inch to 0.600 inch. With the diameter of the barbs being 0.200 inch in diameter, a snap-in fit is ensured in the port.

FIG. 5 shows the bottom view of connector 42 having snap-fit barbs 45 at both ends.

FIG. 6 shows an alternate connector 42 affixed to a straight-through internal conduit 44. Connecting barbs 45 are shown for completeness.

Figure 8:
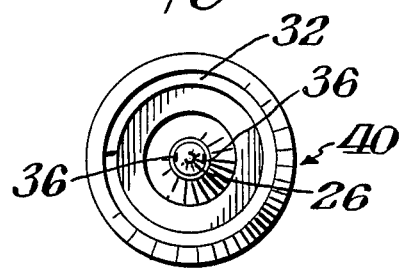
FIG. 8 is a front elevation of the blunt needle assembly.
Figure 9:
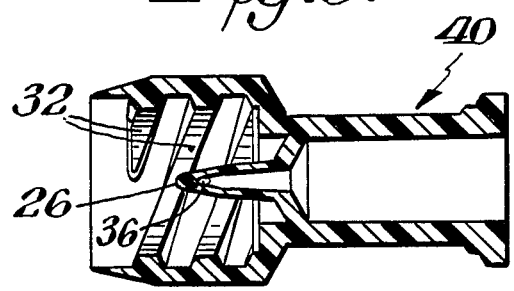
FIG. 9 is a cross-sectional view of the blunt needle assembly taken along the line 9—9 of FIG. 7.

FIGS. 7-9 show the insertion needle assembly 40 in detail, including threads 32 and blunt needle 26.

Figure 10:
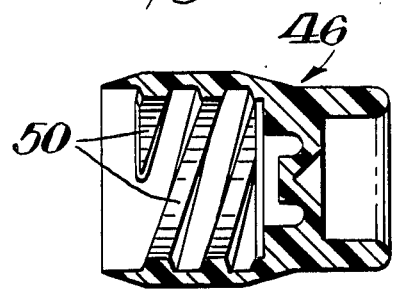
FIG. 10 is a side elevation, partly in corss-section, of a protective cover for the device of this invention.

When the insertion needle assembly 40 is not in use, a protective cap 46 can be attached to the implant device in the same manner as the insertion needle assembly. This is shown in FIG. 10. The protective cap 46 contains internal threads 50 which screw onto the external threaded portion 34 of the mounting ring 22.

Figure 11:
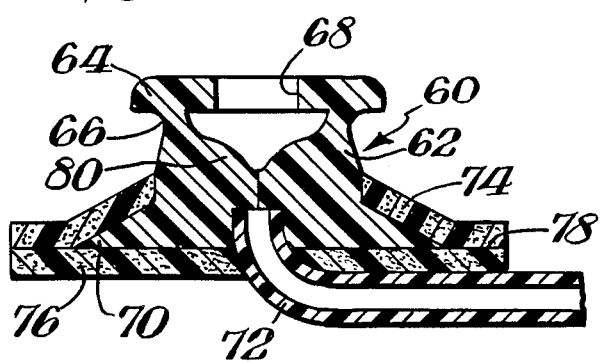
FIG. 11 shows a percutaneous implant device known in the prior art.

Prior art percutaneous implant devices such as that shown in FIG. 11 are known. This device 60 has a housing or "button" 62 having a collar portion 64, a neck portion 66, a lumen 68 and a flange portion 70 as shown. Valve 80 is molded to the button 62 and has an opening 82 therethrough. Silicone tubing 72 and valve 80 are glued together securely. Skirt 74 and bottom flange cover 76 are expanded, porous PTFE and are adhesively affixed to cover the flange, as shown, the overlapping parts being bonded together at line 78.

EXAMPLE 1

A button device was molded from MDX4-4515 elastomer, a material supplied by Dow Corning Corporation of Midland, MI, to the configuration of FIG. 11. The dimensions were as follows: diameter of the collar 0.400 inch, verticle height of the neck 0.120 inch, diameter of the neck at the narrowest portion 0.306 inch. A silicone valve was molded to the lumen of the neck. The height of the valve was 0.060 inch. The valve was punctured with a pin forming an opening therethrough. The button was rinsed with alcohol and de-ionized water to remove the mold release agent and any other contaminates.

A mandrel with a 0.045 inch diameter was placed through the punctured hole in the silicone valve. Silicone tubing, 0.045 I.D., 0.068 O.D., was placed over the mandrel and brought up flush to the bottom of the silicone valve. The tubing was gluded into place using Medical Grade Type "A" silicone adhesive, Dow Corning, Midland, MI. Any excess adhesive was spread flush with the bottom of the silicone flange.

A tube of expanded PTFE having an average fibril length of 125 microns was produced according to the teachings of U.S. Pat. Nos. 4,187,390 and 3,953,566. A mixture of PTFE resin in a liquid lubricant was extruded in tubular form. The extruded tube was dried for approximately 23-24 hours at about 300° C., which also removed the lubricant. The tube was held at a temperature of about 295° C. and it was then stretched longitudinally at a rate of about 75% per second until it was approximately 10 times its original length, where rate was defined as $$\frac{Lf - Li}{Li(t)} \times 100\%$$

and in which Lf=final tube length, Li=initial tube length, and t=total time of stretching. Subsequent to stretching, the tube was restrained longitudinally and heat treated at about 375° C. for about 75 seconds. From the PTFE tube sections, square sections approximately 5 cm×5 cm were cut. The thickness of the material was approximately 0.042 inch. The square to be utilized as the upper skirt 74 had a 0.270 inch diameter hole cut in the center to allow for the skirt to pass over the collar and neck of the button.

The bottom cover material 76 was placed over a base plate of 1.75 inch diameter and secured with a 1.95 inch inner diameter ring. A small slit was made in the cover material to allow the passage of the 0.080 inch diameter silicone tubing.

The top and bottom of the flange were coated with Medical Grade Type "A" adhesive. The upper and lower 5 cm×5 cm PTFE materials 74 and 76 were coated with Medical Grade Adhesive Type "A". The collar and neck were placed through the 0.270 inch hole in the upper skirt. The upper skirt was positioned so that the material fit snugly around the base of the neck where the neck meets the flange. The silicone tubing was placed through the slit in the lower skirt and the lower skirt was brought into laminar contact with the bottom of the flange and the bottom of the upper skirt. The adhesive was allowed to cure for 24 hours. The PTFE material was then cut with a circular cutter which gave the overlapping portions of the PTFE an outer diameter of 0.800 inch.

An insertion needle having an inner diameter of 0.030 inch, an outer diameter of 0.045 inch and a length of 0.110 inch was machined out of Delrin ® polycarbonate. The length of 0.110 inch is utilized to physically open the silicone valve located inside the lumen of the neck of the device. The vertical length of the needle was 0.223 inch and a 90° bend turned the needle to the horizontal for a distance of 0.500 inch. The horizontal portion was 0.250 inch in diameter with an inner diameter of 0.168 inch and having a 2 degree taper to accomodate standard luer lock male connection.

UTILIZATION A

An animal study was performed in an effort to understand some of the theories described in prior art teachings. Three devices prepared in the manner described in Example 1 were implanted in dogs. The silicone tubing sections of the devices were inserted through the right jugular vein with the tip of the tubing resting in the superior vena cava. The devices functioned as a central venous catheter for a period of 30 days. The valving mechanism was similar to the valving mechanism described in U.S. Pat. No. 3,783,868. During the course of the study, it was discovered that the force required to insert the needle through the valve was excessive and disrupting. As force was applied on the vertical portion of the needle to press it through the silicone valve, the entire percutaneous device was forced into the body until it stopped by a resistant factor such as bone. The vertical section of the neck did not possess enough height externally to allow for the button to be grasped while inserting the needle.

All three tubing segments become occluded and redness was observed around all three skin exit sites. The conclusion of the animal study was that the design was impractical for day to day illustration of administering fluids into the body.

EXAMPLE 2

The design of the button device was modified to rectify major problems observed in Utilization A. A conduit device was molded out of MDX4-4515 elastomer. The dimensions of the conduit were as follows: the vertical height of the neck was increased by 0.090 inch and a right angle portion of the conduit was added to the top of the collar, 0.200 inch high from the collar. The total vertical height from the bottom of the flange to the transition point where the bend in the conduit began was increased to 0.530 inch. The bend in the conduit above the collar extended horizontally for a distance of less than about one inch and had a diameter of 0.250 inch. In the lumen of the device at the point where the lumen of the conduit bent 90° and extended down through the neck, a silicone diaphragm was molded across the lumen. A valve was made by leaving a 0.010 inch gap between the horizontal and vertical mandrels which formed the lumen of the port when the device was molded. The thickness of this diaphragm valve was 0.010 inch. A slit was made in the valve approximately 0.060 inch in length by inserting a blade with a width of 0.060 inch up through the lumen from the bottom of the flange and puncturing through the valve.

A flexible convex silicone face valve was molded from MDX4-4515. The diameter of the valve was 0.182 inch and the length was 0.175 inch. The silicone valve was adhered into the end of the right angle external conduit by means of Medical Grade Silicon Adhesive Type "A".

A swivel connector was machined out of polypropylene. The vertical portion of the connector fit into the lumen of the device from the underside of the flange, and this was 0.250 inch in diameter. The overall length of the vertical section was 0.300 inch. Barbs on the vertical section were 0.120 inch in diameter. These barbs allowed the connector to be securely fastened to the port. The horizontal portion of the connector emerged flush with the bottom of the vertical section and had a maximum height of 0.100 inch. The length of the horizontal section was 0.625 inch. The horizontal section contained two barbs having a maximum diameter of 0.110 inch and a 15 degree taper leading to a minimum taper of 0.040 inch. The tapered barbs allowed for the secure fastening of the silicone tubing. The remaining portions of the device were manufactured as in Example 1.

A blunt insertion needle was machined from Delrin ® (Delrin ® is a trademark of E. I. duPont deNemours Co., Inc.). The inner diameter of the needle was 0.030 inch tapering back to an inner diameter of 0.170 inch, a 2 degree taper, to accomodate standard syringes and other luer lock apparatus. The overall length of the needle was 0.635 inch.

UTILIZATION B

Seven devices manufactured according to Example 2 were implanted in canines. The silicone tubing sections of the devices were inserted through the right jugular vein with the tip of the tubing resting in the superior vena cava. The devices functioned as central venous catheters for a period of up to 56 days.

Due to the length of the neck of the device being increased by 0.090 inch and the addition of the right angle exterior extension of the port, the device was handled effectively by the animal study technicians. The ability of the technicians to grasp the device by the right angle exterior extension of the port substantially eliminated the force perpendicular to the skin that caused the device to move as explained in Utilization A.

The silicone diaphram valve located in the lumen of the neck of the device demonstrated its effectiveness in maintaining a secure seal to back pressure and unwanted open exposure from external circumstances. During the study, it was discovered that the flexibility of the silicone elastomer allowed the neck portion of the device to be manipulated so that the slit in the valve could be opened. By opening the valve in this manipulative manner, backbleeding occurred.

The entire port being fabricated of silicone made it extremely difficult to keep the insertion needle assembly and cover cap retained on the port. A satisfactory method of securing a cover cap for the external end was never obtained during this particular animal study.

The following histological observations were made at the conclusion of this animal study. Four of these devices were implanted in canines for 56 days, one for 42 days, and two for 27 and 29 days, respectively. At retrieval, the tissue at the skin exit site of five of the seven devices appeared normal and healthy, with no noticeable gross inflammation. Skin exit site inflammation and serous drainage were noted in the 27 and 29 day retrievals, respectively. A perpendicular downward growth trend of the epidermis towards the flange was noted with all devices. Epidermal downward growth extended to approximately 0.8 mm above the flange on the average. However, in two cases the epidermis did attach to the expanded PTFE material of the flange. The dermis in all cases appeared to be firmly attached to the flange, with healthy dermal tissue observed on both the upper and lower surfaces of the flange. Tissue ingrowth was observed into the PTFE material of the flange. Dense accumulations of fibroblasts were observed within the expanded PTFE material. Moderate to marked collagen was noted within the expanded PTFE material on the lower portion of the flange and minimal to moderate collagen was observed within the upper portion of the flange. Gram positive cocci were observed on the epidermis and within the pilosebaceous units. These gram positive cocci were confined to the immediate region of the skin interface and did not extend into the PTFE material or the surrounding tissues. Although two devices were associated with skin exit site inflammation, skin cultures were negative. The bacterial seal design of the percutaneous device appeared to inhibit infection at the exit site.

Bacterial flushes were performed on six devices during retrieval. All six devices showed no signs of bacterial growth which meant bacteria were not present inside the lumen of the device.

Distal tip cultures were taken from the distal end of the tubing of each device. Two of the six devices reported a slight growth of *Staphylococcus epidermis*, an epidermal bacteria. Since the lumen flushes were performed first and the results were negative, it seemed illogical that the distal tip cultures should report a bacterial infection. Because *Staphylococcus epidermis* is normally found on the epidermis, the conclusion was the slight growth of *Staphylococcus epidermis* was the result of post retrieval contamination.

EXAMPLE 3

The previous device was modified to correct major problems. A method of attaching the needle and cap to the exterior end of the conduit was provided. A point of flexion was developed to aid in the prevention of disruption to the flange tissue ingrowth segment. This device is shown in FIGS. 1-10.

The silicone conduit 12 was molded from MDX4-4515 elastomer. The dimensions were as follows: overall vertical height 0.530 inch, collar diameter 0.360 inch, narrowest diameter of the neck 0.260 inch, base of the neck connecting with flange 0.306 inch, maximum diameter of flange 0.600 inch. The lumen diameter from the collar to the base of the neck, excluding the point of flexion, was 0.100 inch. The lumen diameter at the point of flexion was 0.130 inch for a vertical distance of 0.100 inch. The horizontal exterior section of the conduit 12 possessed an overall length of 0.416 inch from the bend at the collar to the point where mounting ring 22 was bonded. The diameter of the lumen of the horizontal section of the conduit was 0.312 inch. The silicone port conduit was cured for 2 hours at 168° C. in an oven. The silicone conduit was rinsed with alcohol and deionized water to remove contaminates and allowed to dry.

Mounting ring 22 was machined from polycarbonate and had an overall length of 0.563 inch and an outer diameter of 0.312 inch and inner diameter of 0.200 inch. The mounting ring was shipped to Dow Corning, Midland, MI, and was coated by an abrasion resistant coating, ARC®, (ARC® is a registered trademark of Dow Corning). This coating provided a monosiloxane $SiO_2$ coating on the exterior of the mounting ring which allowed medical grade adhesive to bond to the polycarbonate mounting ring.

Right angle swivel connector 42 was machined from polycarbonate material. The inner diameter of the portion which is inserted into the silicone conduit 12 was 0.140 inch. The inner diameter of the external portion, which runs horizontally beneath the bottom flange was 0.040 inch. The length of the external portion which runs horizontally beneath the bottom flange was 0.635 inch. The diameter of the barbs 45 on the portion inserted into the silicone conduit was 0.220 inch. For utilization C, the swivel connector was machined according to FIG. 6.

Silicone face valve 24 was molded out of MDX4-4515. The face was convex having a radius of 0.300 inch for a distance of 0.289 inch. On the reverse side of the convex curvature, the diameter of the valve was 0.198 inch.

The polycarbonate mounting ring 22 was rinsed in Freon® (registered trademark of DuPont) to cleanse it thoroughly. The mounting ring was then dipped in a mixture of 80% adhesive and 20% Freon and allowed to dry. The mounting ring was placed in an oven to cure at 100° C. for 2 hours. Medical Grade Adhesive Type A was spread on the front end portion of the silicone conduit and on the outer diameter of the mounting ring 22. The mounting ring was inserted into the front end portion of the silicone conduit and excessive adhesive was removed. The silicone conduit with the attached mounting ring was placed in an oven to cure at 100° C. for 2 hours.

Medical Grade Adhesive Type A was spread on the inner surface of the mounting ring 22 and on the portion of the face valve to be inserted into the mounting ring. The face valve was then inserted into the mounting ring and the excessive adhesive was removed. The entire device was then placed in an oven to cure at 100° C. for 2 hours.

The face valve 24 was then slit using a blade having a width of 0.080 inch and a thickness of 0.008 inch to make slit 28 in the center of the valve. The connector was inserted into the lumen of the conduit at the bottom of the flange 15.

An insertion needle assembly was machined from polycarbonate material. The overall length of the needle assembly was 0.750 inch, inner diameter of needle assembly 0.314 inch, outer diameter 0.375 inch, width of the threads 0.038 inch, depth of threads 0.022 inch, length of needle 0.240 inch, inner diameter of needle 0.030 inch, wall thickness of needle 0.015 inch and the inner diameter of needle was 0.170 inch with a 2 degree taper.

A protective cover cap 46 was machined from polycarbonate material with the following dimensions: inner diameter 0.314 inch, wall thickness 0.030 inch, width of threads 0.038 inch, depth 0.022 inch, overall length 0.515 inch.

For the purpose of the in vitro bacteria challenge test, the silicone flange 15 was not covered with expanded PTFE.

UTILIZATION C

The purpose of this study was to demonstrate the effectiveness of recommended care techniques in preventing bacterial migration through the face valve of the device of this invention. The effect of eliminating care of the face valve related to risk of bacterial migration was also studied.

The in vitro test was conducted with the catheter device as shown in FIG. 12. The catheter segments were modified for test purposes by securing them with silicone into the mouth of a 16 cc test tube 94 and providing an air port 92 having cotton plug 90 as shown.

Tubing 98 extended into the bottom of the flange of the catheters. Thirty-two catheters 10 were studied. A control group consisting of two catheters was assembled, sterilized, injected with 1 cc of sterile Trypticase soy broth (TSB) 96 and incubated for seven days. The remaining thirty devices were divided into two groups of fifteen each. The face valves of all thirty catheters were challenged daily with a fresh 18-hour "lawn" of *Staphylococcus aureus*. Group one received recommended care techniques outlined in the preceding paragraphs. Group two received no care of the face valve. Following exposure of the face valve to bacteria and performance of recommended care techniques on Group one, all thirty devices were infused using a threaded infusion needle assembly with 1 cc of Trypticase soy broth through the face valve.

Each tube began the experiment containing 1 cc of TSB. Each day, when flushes were performed with a threaded sterile infusion needle assembly inserted through the face valve, an additional 1 cc of TSB was flushed through.

Experimental results were noted on a pass/fail basis, with growth of bacteria in a test tube, which appeared as a cloudy fluid, noted as positive (+) growth, or failure (O) or no growth. As tubes became contaminated, bacterial stains were performed on all cloudy fluids to verify the presence of a Staphylococcus sp. At the end of the test, bacterial stains were performed on all remaining clear tubes.

Thirty-two 16 cc test tubes each with a catheter 10 fixed into their openings with silicone adhesive were used. Seventeen of the thirty-two catheters had the face valve capped with a threaded cap and fifteen of the catheters had no cap on the face valve. Following sterilization, two of the catheters were injected with 1 cc of sterile TSB, capped, set aside and designated as controls. Caps were not removed from these catheter face valves, nor were the face valves exposed to bacteria. The external conduits and flange segments were traced through lot number 0017, Recommended Care Group serial numbers 14, 10, 2, 1, and 15, Recommended Care Group Letters C, E, F, I, J, L, N, Q, S, and U. No Care Group serial numbers 13, 3, 12, 11, and 5, No Care Serial Letters are B, D, G, H, K, M, P, R, T, and V, Control Group serial letters are A and W.

In the testing, a fresh 18-hour lawn of *Staphylococcus aureus* cultured from a standard stock culture of *Staphylococcus aureus* was used. The bacteria were exposed to the Betadine-covered face valves of the Recommended Care devices. According to the Recommended Care treatment, Betadine ointment and bacteria were removed from the face valve with 70% ETOH on a sterile 2"×2" gauze pad. Then the face valves were washed with Betadine solution on a sterile swab for 1 minute. The face valves were then allowed to air dry. A thin film of Betadine ointment was spread over the face valve with a sterile swab and caps were applied.

The No Care devices received no cleaning. Bacteria remained on the face valves. Caps were not applied.

Following the Recommended Care treatment and No Care treatment, sterile threaded insertion needle assemblies were inserted into the face valve of each of the thirty catheters. 1 cc of sterile TSB was infused into each catheter and the Recommended Care devices were then capped with a threaded cap.

For the No Care catheters, following infusion of sterile TSB the infusion needle assembly was removed. No further care was administered to these fifteen No Care catheters. All tubes were incubated at 37° for twenty-four hours. Following twenty-four hour incubation, results were recorded and contamination and infusion were performed again.

Each twenty-four hours, as noted previously, growth or no growth of bacteria in the tubes were recorded on the appropriate chart as + for a cloudy broth or O for a clear broth. The media in all tubes showing positive growth had a Gram stain performed on it. At the end of the experiment, all clear tubes also had a Gram stained performed on them. The stock culture of *Staphylococcus aureus* and broth from failed catheters in the Recommended Care group were analyzed to confirm *Staphylococcus aureus* as the contaminant in the failed catheters.

The purpose of the study was to demonstrate the effectiveness of the Recommended Care technique in preventing bacterial migration through the face valve of the catheter of this invention. The effect of eliminating care of the face valve related to risk of bacterial migration was also studied.

The experiment was run for seven consecutive days and consisted of three groups: Recommended Care—15 face valves, No Care—15 face valves, and controls—2 face valves. The group contained face valves that had been unpunctured, or punctured 1,500, 3,000, 5,000, 7,000, and 10,000 times. All face valves except the controls were exposed to a confluent 18 hour lawn of *Staphylococcus aureus*. After the respective cleaning treatments were performed, the face valves attached to the 16 cc test tubes were injected with 1 cc Trypticase soy broth.

All 15 of the No Care face valves failed after the first day of bacterial contact. At the completion of the study, one (nonpuntured) Recommended Care catheter had failed on the sixth day. All of the 14 remaining external catheter segments demonstrated no sign of bacterial migration through the face valve. The one failed was examined closely. The face valve and slit were cultured to see if any *Staphylococcus aureus* still remained on these parts. After a 48 hour incubation period, no growth of *Staphylococcus aureus* was observed indicating that possibly the failure could have occurred from another source. The contaminated soy broth was analyzed. It demonstrated a heavy growth of *Staphylococcus aureus*. All remaining clear tubes of the Recommended Care catheter were subjected to a gram stain and light microscopy. No bacteria were observed from the clear tubes.

The Recommended Care Technique for cleaning the face valve of the central venous catheter was effective in preventing bacterial migration through face valves punctured as many as 10,000 times. One failure on a nonpunctured valve is unexplained.

The results of the testing using the Recommended Care treatment are summarized in Table 1.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

TABLE 1

| BACTERIAL CHALLENGE OF THE FACE VALVE - CENTRAL VENOUS CATHETER (CVC) | | | | | | | |
|---|---|---|---|---|---|---|---|
| Recommended CVC Group | | DAYS | | | | | |
| | Device No. | 1 | 2 | 3 | 4 | 5 | 6 | 7 |
| 1,500 Punctures | 4 | 0 | 0 | 0 | 0 | 0 | 0 | 0 |
| 3,000 Punctures | 10 | 0 | 0 | 0 | 0 | 0 | 0 | 0 |
| 5,000 Punctures | 2 | 0 | 0 | 0 | 0 | 0 | 0 | 0 |
| 7,000 Punctures | 1 | 0 | 0 | 0 | 0 | 0 | 0 | 0 |
| 10,000 Punctures | 15 | 0 | 0 | 0 | 0 | 0 | 0 | 0 |
| | C | 0 | 0 | 0 | 0 | 0 | 0 | 0 |
| | E | 0 | 0 | 0 | 0 | 0 | 0 | 0 |
| | F | 0 | 0 | 0 | 0 | 0 | + | |
| | I | 0 | 0 | 0 | 0 | 0 | 0 | 0 |
| | J | 0 | 0 | 0 | 0 | 0 | 0 | 0 |
| | L | 0 | 0 | 0 | 0 | 0 | 0 | 0 |
| | N | 0 | 0 | 0 | 0 | 0 | 0 | 0 |
| | Q | 0 | 0 | 0 | 0 | 0 | 0 | 0 |
| | S | 0 | 0 | 0 | 0 | 0 | 0 | 0 |
| | U | 0 | 0 | 0 | 0 | 0 | 0 | 0 |

What is claimed is:

1. A percutaneous implant device to provide a port of entry into the body comprising:
   a nonporous, biocompatible conduit having an upper inlet opening and a lower attached flange, the flange having a top with a continuously curved perimeter and a continuously curved side wall which tapers to a bottom wall having a continuously curved perimeter of larger diameter than said top, and having a central opening therethrough extending from said top through said flange to said bottom wall,
   said conduit extending from the top of the attached flange and having an angle bend above said flange which, in use, extends at an angle to the skin, from the bend location to the conduit inlet, wherein said conduit extends from the top of said flange, first necking inwardly and then flaring outwardly, forming an hourglass configuration and having said angle bend just above said hourglass configuration, and wherein said conduit, within a part of said hourglass portion, has an inside diameter which is larger than the inside diameter of the remainder of said conduit providing a decreased conduit wall thickness at said hourglass configuration.

2. The device of claim 1 wherein said angle bend is substantially a right angle bend.

3. The device of claim 1 wherein said flange is made of a material having pores.

4. The device of claim 1 wherein said flange has an upper skirt and a bottom skirt formed of expanded, porous polytetrafluoroethylene having nodes and fibrils, with average fibril length greater than about 60 microns, to permit ingrowth of epidermal and connective tissue,
   (i) said upper skirt being in laminar contact with and attached to said side wall of said flange, and (ii) said lower skirt being in laminar contact with and attached to said bottom wall and attached to said upper skirt adjacent the perimeter of said bottom wall.

5. The device of claim 4 wherein the expanded, porous polytetrafluoroethylene utilized for the skirt material has average fibril length greater than about 60 microns, a density less than about 1 g/cc, ethanol bubble point less than about 2.0 psi and ethanol mean flow pressure less than about 10 psi.

6. The device of claim 5 wherein the expanded, porous polytetrafluoroethylene utilized for the skirt material has average fibril length greater than or about 100 microns, ethanol bubble point less than about 0.75 psi, ethanol mean flow pressure less than about 3.0 psi and density in the range of about 0.3 to about 0.1 g/cc.

7. The device of claim 4 wherein the expanded, porous polytetrafluoroethylene has average fibril length greater than or about 100 microns.

8. The device of claim 1 having attachment means at said inlet for removably attaching cap means and blunt insertion needle assembly means.

9. The device of claim 8 having cap means removably attached to said inlet opening.

10. The device of claim 9 wherein said cap means are formed of polycarbonate.

11. The device of claim 8 having blunt insertion needle assembly means removably attached to said inlet opening.

12. The device of claim 11 wherein the blunt insertion needle assembly means are formed of polycarbonate.

13. The device of claim 8 wherein said attachment means comprise threads.

14. The device of claim 8 wherein said attachment means are formed of polycarbonate.

15. The device of claim 14 wherein said attachment means have a coating thereon of a monosiloxane $SiO_2$ to promote bonding of polycarbonate to silicone.

16. The device of claim 1 wherein a mechanical connecting apparatus is incorporated in said central opening providing connecting means between the bottom of said flange and an internal conduit.

17. The device of claim 1 having a self-sealing valve in said conduit inlet.

18. The device of claim 1 wherein said conduit and flange are formed of medical grade, biocompatible polydimethylsioxane elastomer.

19. The device of claim 1 wherein connecting means are provided in said central opening to connect said central opening at the bottom of said flange to an internal body conduit wherein said connecting means can swivel.

20. The device of claim 1 wherein a biologically active substance is placed on the flange.

* * * * *